United States Patent [19]

Dankowski

[11] Patent Number: 4,650,612
[45] Date of Patent: Mar. 17, 1987

[54] PROCESS FOR THE PRODUCTION OF MONOPEROXYDICARBOXYLIC ACIDS AND THEIR SALTS

[75] Inventor: Manfred Dankowski, Karlstein, Fed. Rep. of Germany

[73] Assignee: Degussa Aktiengesellschaft, Frankfurt am Main, Fed. Rep. of Germany

[21] Appl. No.: 746,546

[22] Filed: Jun. 19, 1985

[30] Foreign Application Priority Data

Jul. 20, 1984 [DE] Fed. Rep. of Germany ....... 3426792

[51] Int. Cl.$^4$ ........................................... C07C 179/133
[52] U.S. Cl. ................................. 260/502 R; 502/159
[58] Field of Search ..................................... 260/502 R

[56] References Cited

U.S. PATENT DOCUMENTS 2,910,504 10/1959 Hawkinson et al. ............. 260/502 R
2,919,283 12/1959 Greenspan et al. ............. 260/502 R
3,251,862 5/1966 Lidov .............................. 260/502 R

FOREIGN PATENT DOCUMENTS 417480 10/1969 Australia .
276693  7/1983 European Pat. Off. ........ 260/502 R
105689  4/1984 European Pat. Off. ........ 260/502 R
1354160 1/1964 France ............................ 260/502 R
2129034 10/1972 France ............................ 260/502 R
620484  7/1978 U.S.S.R. ......................... 260/502 R

OTHER PUBLICATIONS

Acta Chem. Scand, vol. 12, (1958)6 1337.

Primary Examiner—Natalie Trousof
Assistant Examiner—Bruce D. Gray
Attorney, Agent, or Firm—Cushman, Darby & Cushman

[57] ABSTRACT

The invention is directed to a process for the production of monoperoxydicarboxylic acids and their alkali or alkaline earth metals by reacting the corresponding anhydride with hydrogen peroxide in an organic solvent which dissolves the corresponding peracid and in the presence of an anion exchanger.

30 Claims, No Drawings

PROCESS FOR THE PRODUCTION OF MONOPEROXYDICARBOXYLIC ACIDS AND THEIR SALTS

BACKGROUND OF THE INVENTION

The invention is directed to the production of monoperoxydicarboxylic acids and their salts.

It has long been known to use these compounds as bleaching agents in washing copositions.

There is described in Australian Patent No. 417,480 the improved bleaching action of monoperoxyphthalic acid in the present $Mg^{2+}$ ions in the bleach liquor. The French Patent No. 2,129,034 is direeted to the production of stable monoperoxyphthalic acid from phthalic anhydride and hydrogen peroxide in the presence of 0.01 to 1 mole of magnesium oxide per mole of anhydride. The magnesium salt of the peracid is formed at least in part therefrom and the peracid is precipitated by the addition of a strong mineral acid.

An alkaline acting magnesium compound likewise is necessary according to European patent No. B1-0027693 in order to carry out the oxidation of phthalic anhydride with hydrogen peroxide and simultaneously obtain the magnesium salt of the monoperoxyphthalic acid.

The production of monomperoxyphthalic acid is described in the Acta Chem. Scand. Vol. 12 (1958) 6, page 1331. In order to attain sufficient yield, it is necessary to react the phthalic anhydride at a temperature of below $-5°$ C. with the alkaline oxidation solution. The peracid is separated off after treatment of the solution with sulfuric acid and water by extraction with ether.

The object of the invention is to develop a process of obtaining monoperoxydicarboxylic acids and their salts in a simple manner.

SUMMARY OF THE INVENTION

The invention is directed to a process for the production of monoperoxydicarboxylic acids (hereinafter called percarboxylic acids) and their salts by oxidation of the corresponding anhydrides with hydrogen peroxide in an organic solvent which dissolves the peracid formed comprising carrying out the oxidation in the presence of an anion exchanger, after completing the reaction separating off the anion exchanger and isolating the monoperoxydicarboxylic acid from the solution or precipitating the corresponding salt by addition of an alkaline active alkali or alkaline earth metal salt.

As anhydrides, there are employed compounds of the following formulae;

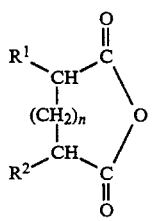
(a) formula (I)

wherein $R^1$ and $R^2$ are the same or different and are hydrogen, linear or branched $C_1-C_{18}$ alkyl, n is 0 or 1 to 10, especially 0 to 2 or 3, preferred are the anhydrides of glutaric acid, succinic acid, and their single alkylated derivatives whose alkyl group contains 1 to 18 carbon atoms,

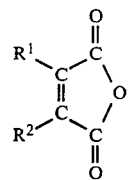
(b) formula (II)

where $R^1$ and $R^2$ are as defined above, preferred are the anhydrides of maleic acid and citraconic acid;

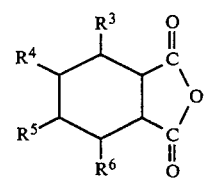
(c) formula (III)

where $R^3$, $R^4$, $R^5$, and $R^6$ are the same or different and are hydrogen, linear, or branched $C_1-C_{10}$ alkyl, the sulfonate or nitro group, chlorine or bromine or $R^3$ and $R^4$ or $R^4$ and $R^5$ or $R^5$ and $R^6$ are eliminated and between the corresponding ring carbon atoms there is a double bond, preferred are the anhydrides of cyclohexane (1,2)-dicarboxylic acid, 4-methylcyclohexane-1,2-dicarboxylic acid, 4-ethyl cyclohexane-1,2-dicarboxylic acid; or (d) formula (IV)

where $R^7$, $R^8$, $R^9$, and $R^{10}$ are the same or different and are hydrogen, linear, or branched $C_1-C_{10}$ alkyl, the sulfonate or nitro group, chlorine or bromine, preferably there is employed the anhydride of o-phthalic acid.

Illustrative of suitable acids whose anhydrides can be used in addition to those mentioned above or in the working examples are oxalic acid, malonic acid, adipic acid, sebacic acid, dodecanedioic acid, dimethyl succinic acid, dibutylsuccinic acid, isopropylsuccinic acid, octadecyl succinic acid, butylmaleic acid, octadecylmaleic acid, 4-decyclohexane (1,2)-dicarboxylic acid, 4,5-dimethyl-cyclohexane (1,2)-dicarboxylic acid, 4-isopropyl-cyclohexane (1,2)-dicarboxylic acid, 4-nitro-cyclohexane (1,2)-dicarboxylic acid, 4-sulfonic acid cyclohexane (1,2)-dicarboxylic acid, 3,4-dichloro-cyclohexane (1,2)-dicarboxylic acid, 3-chlorocyclohexane (1,2)-dicarboxylic acid, 4-bromocyclohexane (1,2)-dicarboxylic acid, 4-cyclohexene-(1,2)-dicarboxylic acid, 3-methylphthalic acid, 4-decylphthalic acid, 3,4-diethylphthalic acid, 4-nitrophthalic acid, benzene-1,2-dicarboxylic acid-4-sulfonic acid, 3-chlorophthalic acid, 4-tromophthalic acid, 3,4-dichlorophthalic acid.

Hydrogen peroxide can be used on the form of aqueous solutions whose peroxide concentration is 20–99%, preferably 40 to 60 weight %.

Especially suited is the illustrative form in which the water content of the oxidation mixture does not lead to the formation of an emulsion with the solvent.

Hydrogen peroxide is employed in the stoichiometric ratio 1:1 to the anhydride. However, a slight excess of up to 0.2 mole, preferably 0.1 mole of hydrogen peroxide is advantageous.

The range of the amount of basic ion exchanger to anhydride is from 0.1 gram to 50 grams, preferably 10 to 20 grams of ion exchanger per mole of anhydride.

The particluar basic ion exchanger is not critical. Preferred are weakly basic anion exchangers with the proviso that they are stable to oxidation.

These specifications can be obtained without difficulty from the brochures of the commerically available ion-exchangers e.g., ion exchange resins.

Illustrative anion exchangers are shown, for example, in the Encyclopedia of Polymer Science and Technology Vol. 7, pages 695 and 697–699 (Interscience Publishers, 1967). Specifically there is recited:

TABLE 1

Manufacturers of Ion Exchange Resins in the United States in 1966

| Company | Location | Trade name |
|---|---|---|
| Diamond Alkali Co. | Redwood City, California | Duolite |
| Dow Chemical Co. | Midland, Michigan | Dowex* |
| Jonac Chemical Co. | Birmingham, New Jersey | Ionac |
| Rohm and Haas Co. | Philadelphia, Pennsylvania | Amberlite |

*The Dowex resins are marketed by the Nalco Chemical Company.

TABLE 2

Commercial Resins Manufactured Outside the United States

| Trade name | Manufacturer |
|---|---|
| Allassion | Dia-Prosim, Vitry-sur-Seine, France |
| Anionite | Soviet Union |
| De-Acidite | The Permutit Co. Ltd., London |
| Diaion | Mitsubishi Chemical Industries, Ltd., Tokyo |
| Imac | Industrieele Maatschappij Activit, Amsterdam |
| Kastel | Montecatini, Milan |
| Kationite | Soviet Union |
| Lewatit | Farbenfabriken Bayer Aktiengesellschaft, Leverkusen, West Germany |
| Wofatit | VEB Farbenfabrik Wolfen, Wolfen Kr. Bitterfeld East Germany |
| Zeo-Karb | The Permutit Co., Ltd., London |

Classification

More than one hundred synthetic ion-exchange resings are marketed throughout the world. These may be broadly classified as cation- and anion-exchange materials which contain fixed anionic and cationic groups, respectively. The cation-exchange resins are subclassified into strong-acid and weak-acid types; similarly, the anion-exchange resins are divided into strong-base and weak-base materials. The active groups associated with each of these classifications are listed in Table 4.

TABLE 3

| Trade name | Matrix | Structure | Active group | Particle shape | Total capacity eq/l | meq/g |
|---|---|---|---|---|---|---|
| Strong-base anion-exchange resins[b] | | | | | | |
| Allassion AQ217 | polystyrene | gel | $-N^{\oplus}(CH_2)_2Cl^{\ominus}$ | spherical | 1.3 | 3.2 |
| Amberlite IRA-400 | polystyrene | gel | $-N^{\oplus}(CH_2)_2Cl^{\ominus}$ | spherical | 1.4 | 3.3 |
| Amberlite IRA-900 | polystyrene | macroporous | $-N^{\oplus}(CH_2)_2Cl^{\ominus}$ | spherical | 1.0 | 3.0 |
| Amberlite IRA-904 | polystyrene | macroporous | $-N^{\oplus}(CH_2)_2Cl^{\ominus}$ | spherical | 0.7 | |
| Anionite AV-17 | polystyrene | gel | $-N^{\oplus}(CH_2)_2Cl^{\ominus}$ | spherical | | |
| De-Acidite FF(IP) | polystyrene | "isoporous" | $-N^{\oplus}(CH_2)_2Cl^{\ominus}$ | spherical | 1.2 | 4.0 |
| Diaion SA-10A | polystyrene | gel | $-N^{\oplus}(CH_2)_2Cl^{\ominus}$ | spherical | 1.4 | 3.4 |
| Dowex 1 | polystyrene | gel | $-N^{\oplus}(CH_2)_2Cl^{\ominus}$ | spherical | 1.4 | 3.5 |
| Dowex 21K | polystyrene | gel | $-N^{\oplus}(CH_2)_2Cl^{\ominus}$ | spherical | 1.3 | 4.2 |
| Duolite A-101D | polystyrene | semiporous | $-N^{\oplus}(CH_2)_2Cl^{\ominus}$ | spherical | 1.4 | 4.2 |
| Duolite A-111 | polystyrene | semiporous | $-N^{\oplus}(CH_2)_2Cl^{\ominus}$ | spherical | 1.0 | 4.2 |
| ImacS5-40 | polystyrene | macroporous | $-N^{\oplus}(CH_2)_2Cl^{\ominus}$ | spherical | 1.1 | 3.4 |
| ImacS5-5- | polystyrene | gel | $-N^{\oplus}(CH_2)_2Cl^{\ominus}$ | spherical | 1.3 | 3.6 |
| Kastel A-500 | polystyrene | gel | $-N^{\oplus}(CH_2)_2Cl^{\ominus}$ | spherical | 1.2 | 3.3 |
| Ionac A-540 | polystyrene | gel | $-N^{\oplus}(CH_2)_2Cl^{\ominus}$ | spherical | 1.3 | 3.6 |
| Lewatit M-500 | polystyrene | gel | $-N^{\oplus}(CH_2)_2Cl^{\ominus}$ | spherical | 1.4 | 3.6 |
| Lewatit MP-500 | polystyrene | macroporous | $-N^{\oplus}(CH_2)_2Cl^{\ominus}$ | spherical | 1.1 | 3.6 |
| Wofatit SBW | polystyrene | gel | $-N^{\oplus}(CH_2)_2Cl^{\ominus}$ | spherical | 1.3 | 3.5 |
| Allassin AQ227 | polystyrene | gel | $-N^{\oplus}(CH_2)_2(C_2H_4OH)Cl^{\ominus}$ | spherical | 1.4 | 3.4 |
| Amberlite IRA-410 | polystyrene | gel | $-N^{\oplus}(CH_2)_2(C_2H_4OH)Cl^{\ominus}$ | spherical | 1.4 | 3.5 |
| Amberlite IRA-910 | polystyrene | macroporous | $-N^{\oplus}(CH_2)_2(C_2H_4OH)Cl^{\ominus}$ | spherical | 1.1 | |
| Diaion SA-20A | polystyrene | gel | $-N^{\oplus}(CH_2)_2(C_2H_4OH)Cl^{\ominus}$ | spherical | 1.4 | 3.5 |
| Dowex 2 | polystyrene | gel | $-N^{\oplus}(CH_2)_2(C_2H_4OH)Cl^{\ominus}$ | spherical | 1.4 | 3.5 |
| Duolite A-102D | polystyrene | semiporous | $-N^{\oplus}(CH_2)_2(C_2H_4OH)Cl^{\ominus}$ | spherical | 1.4 | 3.6 |
| Imac S 5-52 | polystyrene | macroporous | $-N^{\oplus}(CH_2)_2(C_2H_4OH)Cl^{\ominus}$ | spherical | 1.3 | 3.4 |
| Ionac A-550 | polystyrene | gel | $-N^{\oplus}(CH_2)_2(C_2H_4OH)Cl^{\ominus}$ | spherical | 1.3 | 3.4 |
| Kastel A-300 | polystyrene | gel | $-N^{\oplus}(CH_2)_2(C_2H_4OH)Cl^{\ominus}$ | spherical | 1.2 | 3.1 |
| Lewatit M-600 | polystyrene | gel | $-N^{\oplus}(CH_2)_2(C_2H_4OH)Cl^{\ominus}$ | spherical | 1.4 | 3.6 |
| Lewatit MP-600 | polystyrene | macroporous | $-N^{\oplus}(CH_2)_2(C_2H_4OH)Cl^{\ominus}$ | spherical | 1.1 | 3.3 |
| Weak-base anion-exchange resins[c] | | | | | | |
| Allassion A33-03 | polystyrene | "equiporous" | $-NR:$ | spherical | 1.2 | |
| Amberlite IRA-45 | polystyrene | "equiporous" | $-NR_2, -NHR, -NH:$ | spherical | 2.3 | 5.6 |
| Amberlite IRA-93 | polystyrene | macroporous | $-NR_2$ | spherical | 1.4 | |
| De-Acidite G | polystyrene | gel | $-N(C_2H_2)_2$ | spherical | 1.6 | 4.0 |
| De-Acidite M | polystyrene | gel | $-NR_2, -NHR, -NH_2$ | spherical | 2.2 | 5.8 |
| Dowex 3 | polystyrene | gel | $-NR_2, -NHR, -NH_2$ | spherical | 2.6 | 5.8 |
| Imac A-20 | polystyrene | macroporous | $-NR_2, -NHR, -NH_2$ | spherical | 2.3 | |
| Imac A-21 | polystyrene | macroporous | $-NR_2$ | spherical | 1.6 | |
| Ionac A-315 | polystyrene | macroporous | $-NR_2, -NHR, -NH_2$ | spherical | 2.3 | 5.6 |
| Lewatit MP-60 | polystyrene | macroporous | $-NHR, -NR_2$ | spherical | 2.2 | 5.8 |
| Allassion AWB-3 | epoxy-amine | gel | $-NR_2, -N^{\oplus}R_3$ | spherical | 1.9 | 8.2 |
| Anionite EDE-10P | epoxy-amine | gel | $-NR_2, -NHR, -N^{\oplus}R_3$ | spherical | | |
| Anionite AV-16 | epoxy-amine | gel | $-NHR, -NR_2, -NC_6H_5R$ | spherical | | |

| | | | -continued | | | |
|---|---|---|---|---|---|---|
| Dowex 44 | epoxy-amine | gel | —NHR, —NR$_2$ | clusters | 2.4 | 8.5 |
| Duolite A-30B | epoxy-amine | gel | —NR$_2$, —N$^{\oplus}$R$_3$ | spherical | 2.5 | 8.6 |
| Duolite A-57 | epoxy-amine | gel | —NR$_2$, —N$^{\oplus}$R$_3$ | spherical | 2.2 | 8.7 |
| Imac | epoxy-amine | gel | —NR$_2$, —N$^{\oplus}$R$_3$ | spherical | 2.5 | 8.5 |
| Ionac A-300 | epoxy-amine | gel | —NR$_2$, —N$^{\oplus}$R$_3$ | granular | 2.5 | 8.6 |
| Ionac A-310 | epoxy-amine | gel | —NR$_2$, —N$^{\oplus}$R$_3$ | spherical | 2.1 | 8.0 |
| Wofatit L-50 | epoxy-amine | gel | —NR$_2$, —N$^{\oplus}$R$_3$ | granular | 2.5 | 8.8 |
| Anionite AN-2F | phenolic | gel | —NHR, —NR$_2$ | granular | | |
| De-Acidite E | phenolic | gel | —NHR, —NR$_2$, —NH$_2$ | granular | 1.0 | 4.5 |
| Duolite A-6 | phenolic | macroporous | —NR$_2$ | granular | 2.4 | 7.3 |
| Duolite A-7 | phenolic | macroporous | —NHR, —NH$_2$ | granular | 2.5 | 9.1 |
| Lewatit MIH 59 | condensate | gel | —NHR, —NH$_2$ | granular | 2.2 | 6.0 |
| Wofatit MD | condensate | gel | —C$_6$H$_4$NH$_2$, —NHR | granular | 2.0 | 5.7 |

$^a$The total capacity applies to the H form.
$^b$The total capacity applies to the Cl form.
$^c$The total capacity applies to the free-base form.

Quaternary ammonium derivatives of this copolymer are in common use as strong-base anion-exchange resins, whereas secondary and tertiary amine derivatives serve as weak-base anion-exchange resins. Phenol-formaldehyde condensates are still used in making strong-acid cation-exchange resins and some rather specialized, but important, weak-base anion-exchange resins. Phenolic resins are sometimes employed for making weak-acid cation-exchange materials, but these are not as widely used as those based on copolymers of acrylic or methacrylic acids or esters or the corresponding nitriles. A third class of polymer, used in making weak-base anion-exchange resins results from the condensation of epichlorohydrin with amines.

TABLE 4

Chemical Classification of Ion-Exchange Resins

| Classification | Active group | Typical configuration |
|---|---|---|
| Anion-exchange resins | | |
| strong base | quaternary ammonium | ⌬—CH$_2$N$^{\oplus}$(CH$_3$)$_3$Cl$^{\ominus}$ |
| weak base | secondary amine | ⌬—CH$_2$NHR |
| weak base | tertiary amine (aromatic matrix) | ⌬—CH$_2$NR$_2$ |
| weak base | tertiary amine (aliphatic matrix) | —CHCH$_2$NCH$_2$—<br>      \|      \|<br>      OH  CH$_2$<br>             \| |

The use of the ion exchanger in contrast to the process according to the state of the art makes possible the continuous production of the peracids of the invention, by, e.g., bringing the reaction mixture into contact with the ion exchanger over a sufficiently long stretch.

With the process of the invention, there is formed directly the monoperoxycarboxylic acid without the presence of the customary basic salts such as, e.g., alkali or alkaline earth hydroxides or basic carbonates and without addition of mineral acids.

The production of these peroxyacids was previously made difficult by the fact that most suitable point in time for acidifying the reaction mixture could not be predicted exactly.

If a salt of the peracid is desired, there is added after the separation of the ion exchanger to the remainder of the reaction solution an alkali or alkaline earth oxide, preferably a magnesium compound, in an amount theoretically sufficient to neutralize the remaining carboxy group and preferably in an excess of 1%. The especially suited magnesium hydroxide is used in a mole ratio of at least 1:2 based on the peracid.

Especially suited are magnesium hydroxide/peracid mole ratios of 1:2 to 1.1:2. Other alkali or alkaline earth compounds include, for example, magnesium oxide, magnesium carbonate, calcium hydroxide, calcium oxide, barium hydroxide, sodium hydroxide, sodium oxide, sodium carbonate, potassium hydroxide, potassium oxide, and potassium carbonate.

In the case of the monoperoxyphthalic acid, there is formed the hydrated salt.

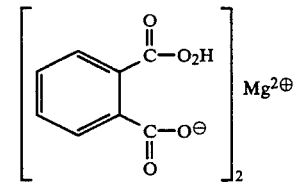

The sequence of addition of anhydride to the organic solvent is not decisive.

However, it is important that the temperature in the reaction of anhydride and hydrogen peroxide be controlled. The rection temperature is in the range of $-10°$ C. to $+50°$ C., preferably $0°$ C. to $20°$ C., especially $10°$ to $20°$ C.

Reaction times of 5 minutes to 5 hours, preferably 10 minutes to 1 hour, are employed.

The reaction between the alkaline, alkali, or alkaline earth metal compound and the monoperoxydicarboxylic acid formed is preferably carried out between $15°$ C. and $20°$ C. with a reaction time of 2 to 20 minutes.

The salt of the peracid formed is separated off subsequently according to the rules of the art, e.g., via a filter of centrifuge. It is preferred to wash subsequently with a non-aqueous solvent in order to dissolve out any residual anhydride which might be present.

As organic solvent, there is employed a low molecular weight aliphatic ester, preferably an acetate and especially ethyl acetate. Other solvents include alkyl alkanoates such as methyl acetate, propyl acetate, butyl acetate, methyl propionate, ethyl propionate, and methyl butyrate.

The anhydride employed must at least be dissolved, the alkali or alkaline earth metals salts of the peracid do not dissolve in the solvent employed.

The process can comprise, consist essentially of, or consist of the recited steps with the stated material.

DETAILED DESCRIPTION

EXAMPLE 1

25 grams of phthalic anhydride were dissolved in 150 ml of ethyl acetate and cooled to 10° C. Then there were added 3 grams of Lewatit MP 62. Subsequently, within 15 minutes, there were dropped in at the same temperature with stirring 11.5 grams of 50 wt. % hydrogen peroxide. Stirring was contained for 1 hour, whereby the temperature of the mixture increased to about 20° C. Then there was separated off the ion exchanger and there were obtained from the solution 25.4 grams of monoperoxyphthalic acid having an AO content of 7.0%.

EXAMPLE 2

25 grams of phthalic anhydride were dissolved in 150 ml of ethyl acetate and cooled to 10° C. Then there were added 3 grams of Lewatit MP 62. Subsequently, within 15 minutes, there were dropped in with stirring 11. 5 grams of 50 wt. % hydrogen peroxide at the same temperature. Then the mixture was stirred for 1 more hour whereby the temperature of the mixture increased to about 20° C. Then there was separated off the ion exchanger and after neutralization with 5 grams of magnesium hydroxide at 20° C. in 15 minutes and drying there were obtained 31 grams of hydrated monoperoxyphthalic acid mono Mg salt having an AO Content of 5.1%.

EXAMPLE 3

25 grams of phthalic anhydride were dissolved in 150 ml of ethyl acetate and cooled to 10° C. Then there were added 3 grams of Lewatit MP 62. Subsequently, within 15 minutes, there were dropped in at the same temperature with stirring 11.5 grams of 50 wt. % hydrogen peroxide. Then the mixture was stirred for a further 3 hours whereby the temperature of the mixture increased to about 20° C. Then the ion exchanger was separated off and after neutralization with 5 grams of magnesium hydroxide at 20° C. in 15 minutes and drying there were obtained 27 grams of hydrated monoperoxyphthalic acid mono Mg salt with an AO content of 5.4%.

EXAMPLE 4

25 grams of phthalic anhydride were dissolved in 150 ml of ethyl acetate and tempered at 20° C. Then there were added 3 grams of Lewatit MP 62. Subsequently, within 15 minutes, there were dropped in with stirring at the same temperature 11.5 grams of 50 wt. % hydrogen peroxide. Then the mixture was further stirred for 1 hour at this temperature. Then the ion exchanger was separated off and after neutralization with 5 grams of magnesium hydroxide at 20° C. in 15 minutes and drying there were obtained 23 gram of hydrated monoperoxyphthalic acid mono-Mg salt having an AO content of 5.2%.

EXAMPLE 5

25 grams of phthalic anhydride were dissolved in 100 ml of ethyl acetate and tempered at 20° C. Then there were added 3 grams of Lewatit MP 62. Subsequently, within 15 minutes, there were dropped in at the same temperature with stirring 11.5 grams of 50 wt. % hydrogen peroxide. The mixture was stirred for 1 more hour at 30° C. Then the ion exchanger was separated off and after neutralization with 5 grams of magnesium hydroxide at 20° C. in 15 minutes and drying there were obtained 25 grams of hydrated monoperoxyphthalic acid mono Mg salt having an AO content of 5.2%.

EXAMPLE 6

25 grams of phthalic anhydride were dissolved in 150 ml of ethyl acetate and cooled to 10° C. Then there was added 1 gram of Lewatit MP 62. Subsequently, within 15 minutes, at the same temperature with stirring there were dropped in 11.5 grams of 50 wt. % hydrogen peroxide, Stirring was continued for 1 more hour, whereby the temperature of the mixture increased to about 20° C. Then the ion exchanger was separated off and after neutralization with 5 grams of magnesium hydroxide at 20° C. in 15 minutes and drying there were obtained 25 grams of hydrated monoperoxyphthalic acid mono Mg salt having an AO content of 5.4%.

EXAMPLE 7

25 grams of phthalic anhydride were dissolved in 150 ml of ethyl acetate and cooled to 10° C. Then there were added 3 grams of Lewatit MP 62. Subsequently, within 15 minutes, at the same temperature with stirring there were dropped in 11.5 grams of 50 wt. % hydrogen peroxide. Then stirring was continued for 1 hour, whereby the temperature of the mixture increased to about 20° C. Then the ion exchanger was separated off and after neutralization with 3.4 grams of magnesium oxide at 20° C. in 15 minutes and drying there were obtained 23 grams of hydrated monoperoxyphthalic acid mono Mg salt having an AO content of 5.2%.

EXAMPLE 8

25 grams of phthalic anhydride were dissolved in 150 ml of ethyl acetate and cooled to 10° C. Then there were added 3 grams of Lewatit MP 62. Subsequently, within 15 minutes, at the same temperature and with stirring there were dropped in 11.5 grams of 50 wt. % hydrogen peroxide. Then stirring was continued for 1 hour whereby the temperature of the mixture increased to about 20° C. Then the ion exchanger was separated off and after neutralization with 9.8 grams of basic magnesium carbonate at 20° C. in 15 minutes and drying there were obtained 12 grams of hydrated monoperoxyphthalic acid mono Mg salt having an AO content of 2.3%.

EXAMPLE 9

25 grams of phthalic anhydride were dissolved in 150 ml of ethyl acetate and cooled to 10° C. Then there were added 3 grams of Lewatit MP 62. Subsequently, within 15 minutes, at the same temperature and with stirring there were dropped in 20 grams of 30 wt. % hydrogen peroxide. Then stirring was continued for 1 hour, whereby the temperature of the mixture increased to about 20° C. Then the ion exchanger was separated off and after neutralization with 5 grams of magnesium hydroxide at 20° C. in 15 minutes and drying there were obtained 18 grams of hydrated monoperoxyphthalic acid mono Mg salt having an AO content of 4.9%.

EXAMPLE 10

25 grams of phthalic anhydride were dissolved in 100 ml of ethyl acetate and cooled to 10° C. Then there were added 3 grams of Lewatit MP 62. Subsequently, within 15 minutes, at the same temperature and with stirring there were dropped in 15 grams of 40 wt. % hydrogen peroxide. Then stirring was continued for 1 hour, whereby the temperature of the mixture increased to about 20° C. Then there was separated off the ion exchanger and after neutralization with 5 grams of magnesium hydroxide at 20° C. in 15 minutes and drying there were obtained 25 grams of hydrated monoperoxyphthalic acid mono Mg salt having an AO content of 5.3%.

EXAMPLE 11

16.7 grams of maleic anhydride were dissolved in 150 ml of ethyl acetate and cooled to 0° C. Then there were added 3 grams of Lewatit MP 62. Subsequently, within 10 minutes, at the same temperature and with stirring there were dropped in 11.5 grams of 50 wt. % hydrogen peroxide. Then stirring was continued for 1 hour, whereby the temperature was held between 0° and 5° C. Then there was separated off the ion exchanger and there were obtained from the solution 16 grams of monoperoxymaleic acid having an AO content of 10.8%.

EXAMPLE 12

19.4 grams of glutaric anhydride were dissolved in 150 ml of ethyl acetate and cooled to 10° C. Then there were added 3 grams of Lewatit MP 62. Subsequently, within 5 minutes, at the same temperature and with stirring, there were dropped in 11.5 grams of 50 wt. % hydrogen peroxide. Then stirring was continues for 1 hour whereby the temperature of the mixture increased to about 20° C. Then there was separated off the ion exchanger and there were obtained from the solution 21 grams of monoperoxyglutaric acid having an AO content of 5.7%.

EXAMPLE 13

26.2 grams of cyclohexane-1,2-dicarboxylic acid anhydride were dissolved in 150 ml of ethyl acetate and cooled to 10° C. Then there were added 3 grams of Lewatit MP 62. Subsequently, within 5 minutes at the same temperature and with stirring, there were dropped in 11.5 grams of 50 wt. % hydrogen peroxide. Then stirring was continued to 1 hour, whereby the temperature increased to about 20° C. Then there was separated off the ion exchanger and there were obtained from the solution 25 grams of monoperoxycyclohexane-1,2-dicarboxylic acid having an AO content of 4.0%.

EXAMPLE 14

28.6 grams of 4-methylcyclohexane, 1,2-dicarboxylic acid anhydride were dissolved in 150 ml of ethyl acetate and cooled to 10° C. Then there were added 3 grams of Lewatit MP 62. Subsequently, within 5 minutes, at the same temperature and with stirring there were dropped in 11.5 grams of 50 wt. % hydrogen peroxide. Then stirring was continued for 1 hour whereby the temperature increased to about 20° C. Then there was separated off the ion exchanger and there were obtained from the solution 28 grams of monoperoxy-4-methylcyclohexane-1,2-dicarboxylic acid having an AO content of 4.0%.

EXAMPLE 15

36.1 grams of octylsuccinic acid anhydride were dissolved in 150 ml of ethyl acetate and cooled to 10° C. Then there were added 3 grams of Lewatit MP 62. Subsequently, within 5 minutes, at the same temperature and with stirring, there were dropped in 11.5 grams of 50 wt. % hydrogen peroxide. Then stirring was continued for 1 hour, whereby the temperature increased to about 20° C. Then the ion exchanger was separated off and there were obtained from the solution 37 grams of monoperoxy-2-octylsuccinic acid having an AO content of 3.5%.

EXAMPLE 16

14.8 grams of tetradecylsuccinic acid anhydride were dissolved in 100 ml of ethyl acetate and cooled to 10° C. Then there was added 1 gram of Lewatit MP 62. Subsequently, within 10 minutes, at the same temperature and with stirring, there were dropped in 3.4 grams of 50 wt. % hydrogen peroxide. Then stirring was continued for 3 hours, whereby the temperature increased to about 20° C. Then the ion exchanger was separated off and there were obtained from the solution 9 grams of monoperoxy-2-tetradecylsuccinic acid having an AO content of 2.7.

The entire disclosure of German priority application No. P.3426792.1 is hereby incorporated by reference.

What is claimed is:

1. In a process for the production of a monoperoxydiacarboxylic acid or an alkali metal or alkaline earth metal salt thereof by oxidizing the corresponding anhydride in the presence of an anion exchange resin with hydrogen peroxide in an organic solvent stable to the peracid formed, the improvement comprising carrying out the oxidation in the presence of an anion exchange resin and separating off the anion exchange resin after the reaction.

2. A process according to claim 1 including the step of isolating the monoperoxydicarboxylic or salt thereof from the solvent.

3. A process according to claim 2 comprising after removal of the anion exchange resin adding to the solution of monoperoxy dicarboxylic acid in the solvent an alkaline acting alkali metal or alkali metal compound in an amount sufficient to neutralize the non-peroxidized carboxyl group and precipitate the corresponding mono salt of the monoperoxydicarboxylic acid from solution.

4. A process according to claim 3 wherein there is employed an alkaline acting magnesium compound.

5. A process according to claim 2 comprising recovering the free monoperoxydicarboxylic acid.

6. A process according to claim 2 wherein the anhydride employed has one of the following formulae;

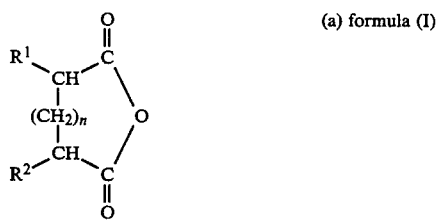

(a) formula (I)

wherein $R^1$ and $R^2$ are hydrogen, $C_1$–$C_{18}$ alkyl, n is an integer from 0 to 10;

(b) formula (II)

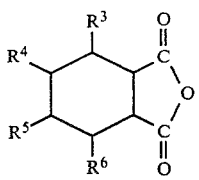
(c) formula (III)

were $R^3$, $R^4$, $R^5$, and $R^6$ are hydrogen, $C_1$-$C_{10}$ alkyl, the sulfonate or nitro group, chlorine or bromine or $R^3$ and $R^4$ or $R^4$ and $R^5$ or $R^5$ and $R^6$ are eliminated and between the corresponding ring carbon atoms there is a double bond;

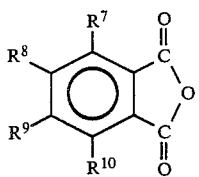
(d) formula (IV)

where $R^7$, $R^8$, $R^9$, and $R^{10}$ are hydrogen, linear, or branched $C_1$-$C_{10}$ alkyl, the sulfonate or nitro group, chlorine or bromine.

7. A process according to claim 6 wherein the anhydride is the anhydride of of glutaric acid, succinic acid, a single alkylated glutaric acid or succinic acid having 1 to 18 carbon atoms in the alkyl group, maleic acid, citraconic acid, cyclohexane-1,2-dicarboxylic acid, 4-methylcyclohexane-1,2-dicarboxylic acid, 4-ethylcyclohexane-1,2-dicarboxylic acid or o-phthalic acid.

8. A process according to claim 7 wherein the anhydride is phthalic anhydride, maleic anhydride, glutaric anhydride, cyclohexane-1,2-dicarboxylic acid anhydride, 4-methylcyclohexane-1,2-dicarboxylic acid anhydride, octylsuccinic acid anhydride or tetradecylsuccinic acid anhydride.

9. A process according to claim 8 wherein the solvent is ethyl acetate.

10. A process according to claim 8 wherein the anhydride is phthalic anhydride and the monoperoxyphthalic acid formed is converted to the magnesium salt by reacting with magnesium hydroxide, magnesium oxide, or basic magnesium carbonate.

11. A process according to claim 6 wherein there is employed phthalic anhydride.

12. A process according to claim 1 wherein the peracid is formed at −10° C. to +50° C. in a reaction time of 5 minutes to 5 hours with a hydrogen peroxide/anhydride mole ratio of 1:1 to 1:2.

13. A process according to claim 6 wherein the peracid is formed at −10° C. to +50° C. in a reaction time of 5 minutes to 5 hours with a hydrogen peroxide/anhydride mole ratio of 1:1 to 1:2.

14. A process according to claim 7 wherein the peracid is formed at −10° C. to +50° C. in a reaction time of 5 minutes to 5 hours with a hydrogen peroxide/anhydride mole ratio of 1:1 to 1:2.

15. A process according to claim 13 wherein the temperature is 0° to 20° C., the reaction time is 10 minutes to 1 hour, the hydrogen peroxide to anhydride mole is 1.1:1 and the solvent is ethyl acetate.

16. A process according to claim 14 wherein the temperature is 0° to 20° C., the reaction time is 10 minutes to 1 hour, the hydrogen peroxide to anhydride mole is 1.1:1 and the solvent is ethyl acetate.

17. A process according to claim 2 comprising forming the magnesium salt of the monoperoxycarboxylic acid by adding an alkaline acting inorganic magnesium compound to the solution of monoperoxycarboxylic acid.

18. A process according to claim 6 comprising forming the magnesium salt of the monoperoxycarboxylic acid by adding an alkaline acting inorganic magnesium compound to the solution of monoperoxycarboxylic acid.

19. A process according to claim 18 wherein there is employed magnesium hydroxide and monoperoxycarboxylic acid in the molar ratio of 1:2 and 1.1:2.0.

20. A process according to claim 17 wherein there is employed magnesium hydroxide and monoperoxycarboxylic acid in the molar ratio of 1:2 and 1.1:2.0.

21. A process according to claim 1 wherein the ratio of anion exchange resin to anhydride is from 0.1 gram to 50 grams per mole of anhydride.

22. A process according to claim 2 wherein the ratio of anion exchange resin to anhydride is from 0.1 gram to 50 grams per mole of anhydride.

23. A process according to claim 6 wherein the ratio of anion exchange resin to anhydride is from 0.1 gram to 50 grams per mole of anhydride.

24. A process according to claim 10 wherein the ratio of anion exchange resin to anhydride is from 0.1 gram to 50 grams per mole of anhydride.

25. A process according to claim 11 wherein the ratio of anion exchange resin to anhydride is from 0.1 gram to 50 grams per mole of anhydride.

26. A process according to claim 15 wherein the ratio of anion exchange resin to anhydride is from 0.1 gram to 50 grams per mole of anhydride.

27. A process according to claim 23 wherein the ratio of anion exchange resin to anhydride is from 10 to 20 grams per mole of anhydride.

28. A process according to claim 24 wherein the ratio of anion exchange resin to anhydride is from 10 to 20 grams per mole of anhydride.

29. A process according to claim 25 wherein the ratio of anion exchange resin to anhydride is from 10 to 20 grams per mole of anhydride.

30. A process according to claim 26 wherein the ratio of anion exchange resin to anhydride is from 10 to 20 grams per mole of anhydride.

* * * * *